United States Patent [19]

Le Govic et al.

[11] Patent Number: 5,834,616
[45] Date of Patent: Nov. 10, 1998

[54] PROCESS FOR THE PRODUCING OF PENTENENITRILES

[75] Inventors: Anne-Marie Le Govic, Paris; Isabelle Storet, Les Eparres, both of France

[73] Assignee: Rhone-Poulenc Fiber & Resin Intermediates, Courbevoie Cedex, France

[21] Appl. No.: 849,923

[22] PCT Filed: Dec. 12, 1995

[86] PCT No.: PCT/FR95/01644

§ 371 Date: Sep. 15, 1997

§ 102(e) Date: Sep. 15, 1997

[87] PCT Pub. No.: WO96/19439

PCT Pub. Date: Jun. 27, 1996

[51] Int. Cl.⁶ .................................................. C07C 253/00
[52] U.S. Cl. ..................................................... 558/311
[58] Field of Search ............................................ 558/311

[56] References Cited

U.S. PATENT DOCUMENTS

| 2,149,280 | 3/1939 | Deem et al. . | |
|---|---|---|---|
| 2,203,861 | 6/1940 | Deem et al. . | |
| 4,743,702 | 5/1988 | Hoelderich et al. | 558/311 |
| 5,138,086 | 8/1992 | Honda et al. | 558/311 |
| 5,352,819 | 10/1994 | Gubelmann et al. | 558/381 |

FOREIGN PATENT DOCUMENTS

| 0 267 438 | 5/1988 | European Pat. Off. . |
|---|---|---|
| 0 571 298A1 | 11/1993 | European Pat. Off. . |
| 1 015 426 | 9/1957 | Germany . |

OTHER PUBLICATIONS

Journal of Organic Chemistry, vol. 36, No. 20, 1971, "Nitrile Synthesis via the Acid–Nitrile Exchange Reaction", pp. 3050–3051.

Liebigs Annalen Der Chemie, vol. 716, 1968, F. Becke et al, Uber die Einwirkung von Carbonsauren auf Nitrile, pp. 78–82.

Chemical Abstracts, vol. 101, No. 3, 16 Jul. 1984, Columbus, Ohio, Abstract No. 22606, Rao et al, p. 529.

Primary Examiner—Johann Richter
Assistant Examiner—Joseph Murray
Attorney, Agent, or Firm—Burns, Doane, Swecker & Mathis, L.L.P.

[57] ABSTRACT

The present invention relates to a process for the preparation of pentenenitriles. In this process the 3- or 4-pentenenitriles are produced by reacting 2-methylglutarimide, ethylsuccinimide, and/or their precursors, such as 4-cyanovalerimide, 2-methyl-4-cyanobutyrimide, 4-cyanovaleric acid, 2-methyl-4-cyanobutyric acid, 3-cyanovalerimide, 2-ethyl-3-cyanopropionimide, 3-cyanovaleic acid, and 2-ethyl-3-cyanopropionic acid, in the vapor phase at temperatures of 200° to 600° C. in the presence of an acidic solid catalyst, such as acidic molecular sieves, acidic clays, bridged or pillared clays, bulk oxides, and acidic phosphates.

17 Claims, No Drawings

PROCESS FOR THE PRODUCING OF PENTENENITRILES

The present invention relates to a process for the preparation of pentenenitriles. Pentenenitriles, more particularly 3-pentenenitrile and 4-pentenenitrile, can result in adiponitrile by reaction with hydrogen cyanide.

The invention more specifically consists of a process for the preparation of pentenenitriles by the use, in the vapour phase, of 2-methylglutarimide and/or of ethylsuccinimide and/or of their precursors, in the presence of an acidic solid catalyst chosen in particular from acidic molecular sieves, acidic clays, bridged clays (or pillared clays), bulk oxides and acidic phosphates.

During the preparation of adiponitrile by hydrocyanation of butadiene, with the intermediate production of pentenenitriles, large amounts of methylglutaronitrile and ethylsuccinonitrile are inevitably obtained. These by-products currently have only very few industrial outlets and must largely be incinerated.

It is therefore entirely desirable to enhance the value of such by-products and this is one of the aims of the present invention. This is because the compounds employed in the present process, 2-methyl-glutarimide and/or ethylsuccinimide, as well as their precursors, can be prepared from methylglutaronitrile or from ethylsuccinonitrile.

2-Methylglutarimide can be employed directly or in the form of one of its precursors, such as in particular 4-cyanovaleramide, 2-methyl-4-cyano-butyramide, 4-cyanovaleric acid or 2-methyl-4-cyanovaleric acid.

Likewise, ethylsuccinimide can be employed directly or in the form of one of its precursors, such as in particular 3-cyanovaleramide, 2-ethyl-3-cyanopropionamide, 3-cyanovaleric acid or 2-ethyl-3-cyanopropionic acid.

2-Methylglutarimide and its precursors are the most important and the preferred substrates among those which can be employed in the present process, in particular because of the higher proportion of methylglutaronitrile available and because of the better results which they provide.

2-Methylglutarimide can be prepared, for example, by reaction of methylglutaronitrile with dodecanoic acid, as described in an article in the Journal of Organic Chemistry, 36, pages 3050 et seq. (1971). It can also be prepared by reaction of methylglutaric acid with ammonia, as described in another article in the Journal of Organic Chemistry, 22, pages 1728 et seq. (1957).

The acidic molecular sieves employed are in particular acidic zeolites of pentasil structure, such as, for example, ZSM-5, ZSM-11, ZSM-12, ZSM-22, ZSM-23, ZSM-48, mordenite or ferrierite, and acidic zeolites of faujasite structure, such as, for example, zeolite X or zeolite Y.

The zeolites of pentasil structure are more particularly zeolites of ZSM-5, ZSM-12, ZSM-11, ZSM-22, ZSM-23, ZSM-48, mordenite and ferrierite type having the general formula (I) expressed in terms of ratios of oxides:

$$M_{2/n}O \cdot X_2O_3 \cdot mSiO_2 \cdot pH_2O \qquad (I)$$

in which:
M represents a component chosen from hydrogen, $NH_4$ and mono-, di-, tri- and tetravalent metals, M being at least in part a hydrogen atom,
X represents a trivalent element chosen from Al, Ga, Fe and B,
n represents a number from 1 to 4,
m represents a number equal to or greater than 2,
p represents a number from 0 to 40.

The zeolites of faujasite structure are more particularly those having the general formula (II) expressed in terms of ratios of oxides:

$$M_{2/n}O \cdot Z_2O_3 \cdot dSiO_2 \cdot xH_2O \qquad (II)$$

in which:
M represents a component chosen from hydrogen, NH4 and mono-, di-, tri- and tetravalent metals, M being at least in part a hydrogen atom,
Z represents a trivalent element chosen from Al, Ga, Fe and B,
n represents a number from 1 to 4,
d represents a number equal to or greater than 2,
x represents a number from 5 to 100.

The zeolites used in the context of the invention are preferably those in the formula (I) or (II) of which the oxide used in combination with silica is that of a trivalent metal, in particular Al or Ga.

Preference is generally given to the acidic zeolites in the formula (I) or (II) of which M is chosen from hydrogen, $NH_4$, alkali metals, such as, for example, Na, K, Li, Rb or Cs, alkaline-earth metals, such as, for example, Be, Mg, Ca, Sr or Ba, rare-earth metals, such as, for example, La or Ce, or transition metals, such as, for example, Fe.

For a more detailed description of acidic clays, reference may be made to Patent FR-A-2,622,575, which is incorporated in the present text by reference.

Preference is given, in the process of the invention, to the use of smectites, such as, for example, montmorillonites, beidellites, nontronites, hectorites, stevensites and saponites.

Bridged clays, which can be used as catalysts in the present process, are clays between the sheets of which have been introduced bridges or pillars which maintain a basal spacing. The basal spacing is the sum of the thickness of a sheet of the clay and of the interfoliar spacing.

The preparation of these bridged clays has been described in particular in Patent FR-A-2,563,446 and in Patent FR-A-2,618,143.

Preference will generally be given, as starting clay, to beidellites.

Bridging of the clays can be achieved in particular using aluminium, vanadium, molybdenum, zirconium, iron, niobium, tantalum, chromium, lanthanum, cerium, titanium and gallium hydroxides or mixed hydroxides of a number of these metals.

These bridged clays can be modified, in particular by the action of a dihalogen, of an ammonium halide or of an acid, such as sulphuric acid or hydrohalic acids. The halogen thus optionally introduced is preferably chlorine or fluorine.

Use is preferably made, in the process of the invention, of clays, particularly beidellites, bridged using aluminium hydroxide.

The bulk oxides are metal oxides, mixtures of metal oxides or modified metal oxides, in particular modified by the action of a dihalogen, of an ammonium halide or of an acid, such as sulphuric acid or hydrohalic acids. The halogen thus optionally introduced is preferably chlorine or fluorine.

Mention may be made, as non-limiting examples, of $SiO_2/Al_2O_3$, $SiO_2/Ga_2O_3$, $SiO_2/Fe_2O_3$ and $SiO_2/B_2O_3$ mixtures, halogenated aluminas, such as in particular chlorinated aluminas and fluorinated aluminas, sulphated zirconia, niobium oxide or tungsten oxide.

The acidic phosphates which can be used in the process of the invention are in particular, by way of examples, boron phosphates, alone or as a mixture with alumina or with silica, corresponding to various $H_3BO_3/H_3PO_4$ molar ratios introduced during the synthesis, lanthanum phosphate, aluminium phosphates corresponding to various $Al_2O_3/H_3PO_4$ molar ratios introduced during the synthesis, phosphorus pentoxide/silica mixtures (generally known as UOP catalysts), aluminophosphates of zeolite structure (AlPO) and silicoaluminophosphates of zeolite structure (SAPO).

The process is implemented continuously.

The catalyst used can be arranged in a stationary bed or be employed in a fluidized bed. It can be used as a mixture with inert solids, in order to increase the contact surface area.

The process is generally implemented at a temperature of 200° C. to 600° C. and preferably of 250° C. to 500° C.

The contact time, defined as the ratio methyl isobutyl ketone, or ethers, such as dibutyl ether or dimethoxyethane. Water can also be used as solvent when precursors of 2-methylglutarimide or of ethylsuccinimide are employed.

They can also be introduced in conjunction with an inert carrier gas; this joint introduction can be carried out in the form of a mixture or in the form of separate simultaneous introductions.

The inert carrier gas can consist of a gas or a mixture of gases which are inert under the reaction conditions, such as, for example, nitrogen or argon.

The substrate employed, in particular 2-methylglutarimide and/or its precursors, represents from 5% to 100% by weight with respect to the total weight of gases introduced into the reaction and preferably from 10% to 100%.

The process of the invention generally results in the formation of a mixture of pentenenitriles, 2-pentenenitrile, 3-pentenenitrile and 4-pentenenitrile. These last two pentenenitriles can be converted into adiponitrile by reaction with hydrogen cyanide.

The following examples illustrate the invention.

The following procedure will be used, except when otherwise mentioned, in the examples.

The following are successively charged, onto the sintered glass, in a reactor arranged vertically (tube made of Pyrex glass with a length=15 cm and with a diameter=2 cm): quartz grains (from 0.63 to 1.25 mm) over a height of 1.2 cm, the catalyst of ZSM-5 type (0.25 cm³, 0.5 cm³, 1 cm³ or 2 cm³, depending on the examples) having a particle size of 0.25–1.25 mm, and then a second layer of quartz with a height of 1.2 cm.

The catalyst is then calcined overnight at 475° C.

The reaction is carried out under a 0.3 liter/hour nitrogen stream at a temperature of 450° C., except when otherwise mentioned.

The dissolved substrate is then injected via a syringe driver.

The injection flow rates will be specified for each example: they are expressed in grams of solution per hour.

After running for approximately 1 hour, the test proper lasts 1 hour, during which the products exiting from the reactor are trapped in a series of three receivers, the first at room temperature and the following ones cooled by ice.

Analysis of the reaction products and of the unconverted substrate is carried out by gas chromatography (GC).

The following are calculated for each test: between the volume of the catalyst and the total gas flow rate (2-methylglutarimide and/or ethylsuccinimide and/or their precursors+solvent, if appropriate+carrier gas, if appropriate) at the chosen temperature, generally varies from 0.1 second to 50 seconds and most often from 0.2 second to 10 seconds.

The pressure is not critical. It is generally between a pressure lower than atmospheric pressure and 10 MPa (100 bar) and preferably between 0.01 MPa (0.1 bar absolute) and 5 MPa (50 bar).

The 2-methylglutarimide and/or the ethylsuccinimide and/or their precursors can be introduced into the reactor containing the catalyst either in the molten state or in solution in a solvent which is substantially inert under the reaction conditions.

Use may be made, as solvents, of any compound which is vaporized under the reaction conditions, which does not induce harmful side reactions and in which the substrate or substrates employed are soluble. In the present text, a substrate is regarded as soluble in a compound when it can be dissolved in the proportion of at least 5 grams per liter of the said compound at 50° C.

Mention may be made, as non-limiting examples of solvents, of nitriles, such as acetonitrile, propionitrile, valeronitrile, adiponitrile or methylglutaronitrile, ketones, such as acetone or the degree of conversion (DC) of the substrate: % of the substrate converted with respect to that which has been charged;

the yields (YY) of pentenenitriles and of methylglutaronitrile formed: molar % of these compounds formed with respect to the substrate charged;

isomeric distribution of the pentenenitriles formed.

EXAMPLES 1 TO 11

These tests were carried out by using 2-methylglutarimide as substrate.

Tests of various acidic zeolites of ZSM-5 type of general formula (I) in which X represents Al and exhibiting various $SiO_2/Al_2O_3$ molar ratios (value of m in the formula (I)):

Zeolite 1

$SiO_2/Al_2O_3=51$

100% of the components M in the formula (I) are H n=1

Zeolite 2

$SiO_2/Al_2O_3=350$

100% of the components M in the formula (I) are H n=1

The operating conditions are those given in the general procedure described above.

The concentration of 2-methylglutarimide in the injected solution is 15% by weight/weight and the injection flow rate of this solution is 3.5 g/h.

The contact time (ct) is indicated (in seconds) for each of the examples.

The results obtained are combined in Table 1 below.

The abbreviations MGI, PN, PN2, PN3, PN4 and MGN used have the following meanings:

MGI=2-methylglutarimide

PN=pentenenitriles

PN2=2-pentenenitrile

PN3=3-pentenenitrile

PN4=4-pentenenitrile

MGN=methylglutaronitrile.

EXAMPLES 12 AND 13

These tests were carried out by using 2-methylglutarimide as substrate.

The operating conditions are those given in the general procedure described above but the tests are carried out at different temperatures.

The concentration of 2-methylglutarimide in the injected solution is 15% by weight/weight and the injection flow rate of this solution is 3.5 g/h.

The catalyst used is zeolite 1 (1 cm$^3$).

The contact time (ct) is indicated for each of the examples.

The results obtained are collated in Table 2 below.

TABLE 1

| Examples | Catalyst (volume) | Solvent | DC % MGI | YY % PN PN2/PN3/PN4 distribution | YY % MGN | ct (in s) |
|---|---|---|---|---|---|---|
| Example 1 | Zeolite 2 (2 cm$^3$) | Acetonitrile | 98 | 75 40/44/16 | 0 | 1.6 |
| Example 2 | Zeolite 2 (1 cm$^3$) | Acetonitrile | 96 | 77 28/53/19 | 6 | 0.8 |
| Example 3 | Zeolite 2 (0.5 cm$^3$) | Acetonitrile | 80 | 65 16/61/23 | 4 | 0.4 |
| Example 4 | Zeolite 2 (0.25 cm$^3$) | acetonitrile | 62 | 47 10/63/27 | 1 | 0.2 |
| Example 5 | Zeolite 1 (0.25 cm$^3$) | Acetonitrile | 79 | 60 15/61/24 | 6 | 0.2 |
| Example 6 | Zeolite 1 (0.5 cm$^3$) | Acetonitrile | 89 | 63 28/52/20 | 9 | 0.4 |
| Example 7 | Zeolite 1 (1 cm$^3$) | Acetonitrile | 99 | 67 41/44/15 | 12 | 0.8 |
| Example 8 | Zeolite 2 (0.5 cm$^3$) | Acetone | 36 | 26 4/60/36 | 1 | 0.5 |
| Example 9 | Zeolite 2 (2 cm$^3$) | Acetone | 68 | 52 11/62/27 | 0 | 1.8 |
| Example 10 | Zeolite 2 (0.25 cm$^3$) | Acetone | 28 | 17 4/59/37 | 0 | 0.2 |
| Example 11 | Zeolite 2 (1 cm$^3$) | Acetone | 50 | 39 7/61/32 | 1 | 0.9 |

TABLE 2

| Examples | Temp. (in °C.) | Solvent | DC % MGI | YY % PN PN2/PN3/PN4 distribution | YY % MGN | ct (in s) |
|---|---|---|---|---|---|---|
| Example 12 | 400 | Acetonitrile | 68 | 41 15/64/21 | 14 | 0.8 |
| Example 13 | 350 | Acetonitrile | 22 | 9 6/71/23 | 9 | 0.8 |

EXAMPLES 14 TO 17

These tests were carried out by using various substrates which are precursors of 2-methylglutarimide:

Example 14, carried out with 4-cyanovaleramide

Example 15, carried out with 2-methyl-4-cyanobutyramide

Example 16, carried out with 4-cyanovaleric acid

Example 17, carried out with 2-methyl-4-cyanobutyric acid.

The operating conditions are those given in the general procedure described above.

The concentration of substrate in the injected solution is 50% by weight/weight and the injection flow rate of this solution is 1 g/h.

The contact time (ct) is indicated for each of the examples.

The results obtained are collated in Table 3 below.

TABLE 3

| Examples | Catalyst (volume) | Solvent | DC % substrate | YY % PN PN2/PN3/PN4 distribution | YY % MGN | ct (in s) |
|---|---|---|---|---|---|---|
| Example 14 | Zeolite 1 (2 cm$^3$) | Water | 82 | 17 51/37/12 | 18 | 2.7 |
| Example 15 | Zeolite 1 (2 cm$^3$) | Water | 81 | 17 52/35/13 | 19 | 2.7 |
| Example 16 | Zeolite 1 (2 cm$^3$) | Acetonitrile | 100 | 17 65/24/11 | 6 | 4.5 |
| Example 17 | Zeolite 2 (2 cm$^3$) | Acetonitrile | 100 | 40 51/37/12 | 11 | 4.5 |

EXAMPLES 18 AND 19

These tests were carried out by using 2-methylglutarimide as substrate.

The operating conditions are those given in the general procedure described above but the tests are carried out with different concentrations of 2-methylglutarimide in the injected solution.

The injection flow rate of these solutions is 3.5 g/h.

The catalyst used is zeolite 2 (0.5 cm$^3$).

The contact time (ct) is indicated for each of the examples.

The results obtained are collated in Table 4 below.

TABLE 4

| Examples | MGI (% w/w) | Solvent | DC % MGI | YY % PN PN2/PN3/PN4 distribution | YY % MGN | ct (in s) |
|---|---|---|---|---|---|---|
| Example 18 | 20 | Acetonitrile | 66 | 55 9/64/27 | 3 | 0.4 |
| Example 19 | 30 | Acetonitrile | 54 | 43 7/64/29 | 2 | 0.4 |

EXAMPLES 20 TO 25

These tests were carried out by using 2-methylglutarimide as substrate and by employing different acidic catalysts.

These catalysts are commercially available products.

Only boron phosphate was prepared in the laboratory, according to the following procedure:

417.4 g of H$_3$PO$_4$ (2.9 mol) are introduced into a 1 l reactor equipped with a central stirrer and a reflux condenser;

then 180 g (2.9 mol) of boric acid H$_3$BO$_3$, sieved at 300 μm, are introduced with stirring;

the mixture is heated at reflux for one hour and is then cooled to room temperature;

the mixture is calcined for 3 h at 500° C.

The operating conditions are those given in the general procedure described above, with a catalyst volume of 1 cm$^3$, a concentration of 2-methylglutarimide in the injected solution of 33% by weight/weight, a nitrogen flow rate of 1 liter/hour and an injection flow rate of 1.5 g/h, acetonitrile being used as solvent.

The contents of the traps are analysed after the first hour of operation.

The results obtained are collated in Table 5 below: degree of conversion (DC) of the substrate and the yield (YY) of pentenenitriles formed.

TABLE 5

| Examples | Catalyst | | DC %<br>MGI | YY %<br>PN |
|---|---|---|---|---|
| Example 20 | $BPO_4$ | B/P = 0.85 | 60 | 27 |
| Example 21 | Mordenite ZM760 | $SiO_2/Al_2O_3 = 25$ | 59 | 25 |
| Example 22 | Zeolite β | $SiO_2/Al_2O_3 = 6$ | 80 | 23 |
| Example 23 | Faujasite HY ZF520 | $SiO_2/Al_2O_3 = 10$ | 61 | 10 |
| Example 24 | Mordenite ZM510 | $SiO_2/Al_2O_3 = 5$ | 44 | 9 |
| Example 25 | HCl-treated montmorillonite | All of $Ca^{2+}$ exchanged | 47 | 7 |

We claim:

1. A process for the preparation of pentenenitriles, said process comprising reacting at least one of 2-methylglutarimide, ethylsuccinimide, and precursors thereof selected from the group consisting of 4-cyanovaleramide, 2-methyl-4-cyanobutyramide, 4-cyanovaleric acid, 2-methyl-4-cyanobutyric acid, 3-cyanovaleramide, 2-ethyl-3-cyanopropionamide, 3-cyanovaleric acid, and 2-ethyl-3-cyanopropionic acid, in the vapor phase, at a temperature of 200° C. to 600° C., in the presence of an acidic solid catalyst selected from the group consisting of acidic molecular sieves, acidic clays, bridged clays (or pillared clays), bulk oxides, and acidic phosphates.

2. The process according to claim 1, wherein 2-methylglutarimide is employed directly or in the form of one of its precursors selected from the group consisting of 4-cyanovaleramide, 2-methyl-4-cyanobutyramide, 4-cyanovaleric acid, and 2-methyl-4-cyanobutyric acid.

3. The process according to claim 1, wherein the acidic molecular sieves employed are zeolites of pentasil structure.

4. The process according to claim 3, wherein the zeolites of pentasil structure are ZSM-5, ZSM-11, ZSM-12, ZSM-22, ZSM-23, ZSM-48, mordenite and ferrierite type having the formula (I) expressed in terms of ratios of oxides:

$$M_{2/n}O \bullet X_2O_3 \bullet mSiO_2 \cdot pH_2O \quad (I)$$

in which:
  M represents a component chosen from hydrogen, $NH_4$ and mono-, di-, tri- and tetravalent metals, M being at least in part a hydrogen atom;
  X represents a trivalent element chosen from Al, Ga, Fe and B;
  n represents a number from 1 to 4;
  m represents a number equal to or greater than 2; and
  p represents a number from 0 to 40.

5. The process according to claim 1 wherein the bulk oxides used are metal oxides, mixtures of metal oxides or metal oxides modified by the action of a dihalogen, of an ammonium halide, or of an acid.

6. The process according to claim 5, wherein the bulk oxides used are selected from $SiO_2/Al_2O_3$, $SiO_2/Ga_2O_3$, $SiO_2/Fe_2O_3$ and $SiO_2/B_2O_3$ mixtures, halogenated aluminas, sulphated zirconia, niobium oxide, and tungsten oxide.

7. The process according to claim 1, wherein the acidic phosphates used are selected from the group consisting of boron phosphates, alone or as a mixture with alumina or with silica, corresponding to various $H_3BO_3/H_3PO_4$ molar ratios introduced during the synthesis, lanthanum phosphate, aluminum phosphates corresponding to various $Al_2O_3/H_3PO_4$ molar ratios introduced during the synthesis, phosphorus pentoxide/silica mixtures, aluminophosphates of zeolite structure (AlPO), and silicoaluminophosphates of zeolite structure (SAPO).

8. The process according to claim 1, which is carried out at a temperature of 250° C. to 500° C.

9. The process according to claim 1, wherein said at least one of 2-methylglutarimide, ethylsuccinimide, and precursors thereof is introduced into a reactor containing the catalyst either in the molten state or in solution in a solvent which is substantially inert under reaction conditions.

10. The process according to claim 9, wherein said at least one of 2-methylglutarimide, ethylsuccinimide, and precursors thereof is introduced into the reactor in solution in a solvent selected from nitrites, ketones, and ethers.

11. The process according to claim 9, wherein a precursor of 2-methylglutarimide or ethylsuccinimide is employed in solution in water.

12. The process according to claim 5, wherein the acid is sulphuric acid or hydrohalic acids.

13. The process according to claim 5, wherein the halogen is chlorine or fluorine.

14. The process according to claim 6, wherein the halogenated aluminas are chlorinated aluminas or fluorinated aluminas.

15. The process according to claim 9, wherein said nitrites are selected from acetonitrile, propionitrile, valeronitrile, adiponitrile, and methylglutaronitrile.

16. The process according to claim 9, wherein said ketones are selected from acetone and methyl isobutyl ketone.

17. The process according to claim 9, wherein said ethers are selected from dibutyl ether and dimethoxyethane.

* * * * *